United States Patent

Brown et al.

[11] Patent Number: 6,156,949
[45] Date of Patent: Dec. 5, 2000

[54] SELECTIVE PSEUDOCUMENE PRODUCTION BY XYLENE METHYLATION

[75] Inventors: Stephen H. Brown, Princeton, N.J.; Mark F. Mathias, Pittsford, N.Y.

[73] Assignee: Mobil Oil Corporation, Fairfax, Va.

[21] Appl. No.: 09/221,548

[22] Filed: Dec. 28, 1998

[51] Int. Cl.[7] ........................................ C07C 2/66
[52] U.S. Cl. ........................ 585/449; 585/447; 585/467
[58] Field of Search .................... 585/447, 449, 585/467

[56] References Cited

U.S. PATENT DOCUMENTS

| | | | |
|---|---|---|---|
| 3,965,209 | 6/1976 | Butter et al. | 260/671 M |
| 4,001,346 | 1/1977 | Chu | 260/671 M |
| 4,067,920 | 1/1978 | Kaeding | 260/671 M |
| 4,356,338 | 10/1982 | Young | 585/407 |
| 4,380,685 | 4/1983 | Chu | 585/466 |
| 4,469,908 | 9/1984 | Burress | 585/467 |
| 4,520,219 | 5/1985 | Sato | 585/462 |
| 4,665,254 | 5/1987 | De Simone | 585/467 |
| 4,891,467 | 1/1990 | Sikkenga | 585/467 |
| 5,004,854 | 4/1991 | Yan | 585/489 |

*Primary Examiner*—Walter D. Griffin

[57] ABSTRACT

There is provided a process for shape selective xylene methylation that involves contacting a feedstream which includes xylene and methanol under alkylation conditions, with a low activity catalyst. Xylene conversions of at least 15% at methanol utilization levels of 25% or greater are achieved by sequential injection of methanol The xylene methylation process has a selectivity for pseudocumene of over 85% and up to 99%, with a pseudocumene:durene ratio of up to 20 or more.

9 Claims, No Drawings

SELECTIVE PSEUDOCUMENE PRODUCTION BY XYLENE METHYLATION

BACKGROUND OF THE INVENTION

The present invention is directed to a process for the selective production of pseudocumene by catalytic methylation of xylene in the presence of a solid catalyst.

Xylenes and higher aromatics such as pseudocumene and mesitylene are desired commercial products having various uses as disclosed in N. E. Ockerbloom's article, "Xylenes and Higher Aromatics" in *Hydrocarbon Processing*, April 1972, pg. 114–118. This article discloses that these products can be obtained through fractional distillation or extraction from $C_9$ aromatic fractions obtained from naphtha cracking or reformate. Pseudocumene may be oxidized to form trimellitic acid which is useful in the manufacture of synthetic fibers and plastics. It may also be desirable to manufacture the acid anhydride form. Thus, there have been efforts to devise processes resulting in a high purity pseudocumene product. Fractionation of an extracted, heavy catalytic reformate containing about 40% pseudocumene to obtain purified pseudocumene requires large fractionation towers to perform the separation. Using a crystalline zeolite catalyst on an extracted reformate cut to increase pseudocumene content has been proposed in U.S. Pat. No. 5,004,854 to Yan.

The term "shape-selective catalysis" describes the catalytic selectivities found in molecular sieves such as zeolites. The principles behind shape selective catalysis have been reviewed extensively, e.g., by N. Y. Chen, W. E. Garwood and F. G. Dwyer, *Shape Selective Catalysis in Industrial Applications*, 36, Marcel Dekker, Inc. Reactant selectivity occurs when a fraction of the feedstock is too large to enter the zeolite pores to react; while product selectivity occurs when some of the products cannot leave the zeolite channels. Product distributions can also be altered by transition state selectivity in which certain reactions cannot occur because the reaction transition state is too large to form within zeolite pores or cages. Another type of selectivity results from configurational restraints on diffusion where the dimensions of the molecule approach that of the zeolite pore system. A small change in the dimensions of the molecule or the zeolite pore can result in large diffusion changes leading to different product distributions.

Several methods have been proposed for the alkylation of aromatic compounds with methanol to produce xylenes, or higher molecular weight aromatics such as trimethylbenzenes or tetramethylbenzenes.

The alkylation of toluene with methanol over cation-exchanged zeolite Y has been described by Yashima et al. in the Journal of Catalysis 16, 273–280 (1970). The selective production of para-xylene was reported over the approximate temperature range of 200 to 275° C., with the maximum yield of para-xylene being observed at 225° C. Higher temperatures were reported to result in a decrease in production of para and ortho-xylenes.

U.S. Pat. No. 3,965,209 to Butter et al. and U.S. Pat. No. 4,067,920 to Kaeding disclose processes for producing para-xylene in low conversion and high selectivity by reaction of toluene with methanol over a zeolite such as ZSM-5. In Butter et al the zeolite is steamed at a temperature of 250–1000° C. for 0.5–100 hours to reduce the acid activity of the zeolite.

U.S. Pat. No. 4,001,346 to Chu relates to a process for the selective production of para-xylene by methylation of toluene in the presence of a catalyst comprising a crystalline aluminosilicate zeolite which has undergone prior treatment to deposit a coating of between about 15 and about 75 wt. % of coke thereon.

U.S. Pat. No. 4,380,685 to Chu relates to the shape selective reactions carried out with zeolite catalysts modified with iron and/or cobalt, and the alkylation of toluene and xylene at temperatures up to 750° C. is disclosed. A zeolite such as ZSM-5 is preferred, and optionally the catalyst is further modified by the incorporation of phosphorus and/or by steaming at a temperature of 250–1000° C.

A process for the methylation of toluene to selectively produce para-xylene is disclosed in International Publication Number WO 98/14415. The process employs a catalyst having a Diffusion Parameter for 2,2-dimethylbutane of about 0.1–15 sec-1. It is disclosed that the required diffisivity for the catalyst can be achieved by severely steaming the catalyst so as to effect a controlled reduction in the micropore volume of the catalyst to not less than 50%, and preferably 50–90%, of that of the unsteamed catalyst.

A process for the selective production of pseudocumene and durene in higher than equilibrium concentrations by methylation of benzene or methyl-substituted benzenes in the presence of AMS-1B crystalline borosilicate at temperatures up to 1000° F. is disclosed in U.S. Pat. No. 4,891,467 to Sikkenga. However, the process produces substantial quantities of durene, resulting in a pseudocumene:durene ratios less than 8:1 in the final product stream.

Another process for the production of pseudocumene over a magnesium modified AMS-1B catalyst is disclosed in U.S. Pat. No. 4,665,254 to De Simone wherein methylation of xylene over the hydrogen form of the catalyst is reported to yield a trimethylbenzene fraction with a high selectivity to pseudocumene. However, pseudocumene selectivity for the patented process decreases both with increased temperature and with a mixed xylenes feed.

It would be desirable to produce a high purity pseudocumene product via a xylene methylation process amenable to a variety of xylene feeds, and operating at high xylene conversions with high utilization of the methanol feedstock to convert xylene into the pseudocumene product. Ideally, such a xylene methylation process would selectively produce 1,2,4 trimethylbenzene (pseudocumene) in lieu of other trimethylbenzene isomers and would also have a high pseudocumene:durene ratio, i.e., the further methylation of trimethylbenzene to tetramethylbenzene would be insubstantial. Thus, the need for complex purification steps to increase the pseudocumene content of the product would be avoided.

SUMMARY OF THE INVENTION

The present invention provides a process for methylation of xylene to selectively form pseudocumene. In the process, the feed comprises xylene and at least two sequential methanol feeds and is contacted with a low activity molecular sieve catalyst under alkylation conditions. The alkylation process of the invention yields a product stream comprising a C9 fraction (pseudocumene (1,2,4 trimethylbenzene), mesitylene (1,3,5 trimethylbenzene), hemimellitene (1,2,3 trimethylbenzene) and orthoethyltoluene) which is greater than 95 mole percent pseudocumene. The selectivity of the process for pseudocumene, with respect to the other two trimethylbenzene isomers, is on the order of at least 90% to 95%, and pseudocumene selectivity of over 99% may be obtained. The process of the invention further provides a product stream comprising a C9+ fraction which is greater than 90 mole percent pseudocumene. Pseudocumene/durene ratios of at least 10 and up to 20 or more are obtained by the process of the present invention. The process of the present invention provides methanol utilization of at least 25% to 30% or more and also single pass xylenes conversion of at least in the range of 15% to 20% or more by the use of methanol injection. The low activity catalyst of the invention may be an intermediate pore size molecular sieve such as ZSM-5 and may be steamed to reduce its activity prior to use in the process of the invention. Catalysts having high silica to alumina ratios on the order of 250 or more may also be used in the process of the invention. The beneficial attributes of the product stream are provided by the process of the invention when xylene:methanol feed ratios are on the order of from at least 4:1 to about 8:1 or more.

DETAILED DESCRIPTION OF THE INVENTION

The present invention relates to a xylene methylation process which provides at least about 85 percent pseudocumene selectivity, preferably at least about 95% pseudocumene selectivity, and most preferably at least about 99% pseudocumene selectivity, relative to the total amount of trimethylbenzene isomers present in the product stream.

In embodiments of the invention, the catalyst used for performing the process of the invention is preferably a medium-pore size aluminosilicate zeolite. Medium pore zeolites are generally defined as those having a pore size of about 5 to about 7 Angstroms, such that the zeolite freely sorbs molecules such as n-hexane, 3-methylpentane, benzene and p-xylene.

The catalytic molecular sieves useful herein have a Constraint Index from about 1 to about 12 and include intermediate pore zeolites as well as other crystalline inorganic materials such as ALPO's or SAPO's. Zeolites which conform to the specified values of Constraint Index for intermediate pore zeolites include ZSM-5, ZSM-11, ZSM-5/ZSM-11 intermediate, ZSM-12, ZSM-22, ZSM-23, ZSM-35, ZSM-48, ZSM-50, and ZSM-57. Such zeolites are described, for example, in U.S. Pat. No. 3,702,886 and Re. No. 29,949, U.S. Pat. Nos. 3,709,979, 3,832,449, 4,046,859, 4,556,447, 4,076,842, 4,016,245, 4,229,424, 4,397,827, 4,640,849, 4,046,685, 3,308,069 and Re. 28,341, to which reference is made for the details of these zeolites. The details of the method by which Constraint Index is determined are described fully in the U.S. Pat. No. 4,016,218, incorporated herein by reference.

The xylene feedstock preferably includes about 50% to 100% xylene, more preferably at least about 80% xylene. The process of the invention obtains high pseudocumene selectivity with xylene feeds comprising a single xylene isomer (i.e., ortho, meta or para) or equilibrium mixtures of isomers. In other embodiments of the invention, non-equilibrium mixtures of xylenes comprising at least two xylene isomers may be used as feed such as a para-depleted effluent stream from a para xylene recovery unit. Other aromatic compounds such as benzene and other alkyl-substituted benzenes may also be present in the xylene feedstock without adversely affecting the present invention.

The catalytic molecular sieves useful in accordance with the methods of the present invention are preferably in the hydrogen form, prior to modification, but may be in the ammonium or sodium form. The crystal size of zeolites used herein is preferably greater than 0.1 micron. The catalyst in the present invention preferably has an alpha value less than 25, preferably less than 10, most preferably less than 1. Further discussion regarding the methods of determining the alpha value and crystal size of a catalyst is available in U.S.

Pat. Nos. 5,406,015, 5,476,823 and 5,659,098 to Beck et al. However, it should be recognized that the alpha value test was not designed to accurately measure the activity of low activity catalysts and therefore alpha value measurements on the catalysts of the invention possess some degree of uncertainty. That is, a catalyst described as having an alpha value of 2 might be more accurately described as having an alpha value in the range of 0.5 to 3.5, or 2±1.5.

Steaming of the porous crystalline material to reduce activity may be effected at a temperature of about 900° C., preferably from about 800° C. to about 1000° C., for a suitable time period effect to an activity reduction, preferably for about 1 hour, and preferably in a manner which can be scaled up to a commerical rotary kiln.

For the process of the invention, the suitable molecular sieve catalyst may be employed in combination with a support or binder material such as, for example, a porous inorganic oxide support, such as alumina, or a clay binder. While the preferred binder is silica, other non-acidic binder materials may be employed, generally in the form of dried inorganic oxide gels or gelatinous precipitates. Suitable clay materials include, by way of example, bentonite, kaolin and kieselguhr. The relative proportion of suitable crystalline molecular sieve to the total composition of catalyst and binder or support may be from about 35% to about 98% by weight binder, and is preferably from about 50% to about 80% by weight of the composition. The composition may be in the form of an extrudate, beads or fluidizable microspheres.

The porous crystalline material may be combined with a binder in the form of a fluidized bed catalyst. This fluidized bed catalyst may comprise clay in the binder thereof, and may be formed by a spray-drying process to form catalyst particles having a particle size of 20–200 microns.

The catalyst of the invention may optionally be precoked. The precoking step is preferably carried out by initially utilizing the uncoked catalyst in the xylene methylation reaction, during which coke is deposited on the catalyst surface and thereafter controlled within a desired range, typically from about 1 to about 20 wt. % and preferably from about 1 to about 5 wt. %, by periodic regeneration by exposure to an oxygen-containing atmosphere at an elevated temperature.

One of the advantages of the catalyst described herein is its ease of regenerability.

Thus, after the catalyst accumulates coke as it catalyzes the xylene methylation reaction, it can easily be regenerated by burning off a controlled amount of coke in a partial combustion atmosphere in a regenerator at temperatures in the range of from about 400° C. to about 700° C. The coke loading on the catalyst may thereby be reduced or substantially eliminated in the regenerator. If it is desired to maintain a given degree of coke loading, the regeneration step may be controlled such that the regenerated catalyst returning to the xylene methylation reaction zone is coke-loaded at the desired level.

The present process may suitably be carried out in fixed, moving, or fluid catalyst beds. If it is desired to continuously control the extent of coke loading, moving or fluid bed configurations are preferred. With moving or fluid bed configurations, the extent of coke loading can be controlled by varying the severity and/or the frequency of continuous oxidative regeneration in the catalyst regenerator.

Preferably, the catalyst contains at least one oxide modifier and more preferably at least one oxide modifier selected from oxides of elements of Groups IIA, IIIA, IIIB, IVA, IVB, VA and VIA of the Periodic Table. Most preferably the oxide modifier is selected from oxides of boron, magnesium, calcium, lanthanum and most preferably phosphorus. It has been unexpectedly discovered that the use of phosphorus in the catalyst of the present invention further improves pseudocumene:durene ratio in the product stream.

Preferably, the catalyst contains about 0.05 to about 20, more preferably about 0.1 to about 10 and most preferably about 0.1 to about 5, wt % of the oxide modifier based on elemental modifier.

Where the modifier includes phosphorus, incorporation of modifier in the catalyst of the invention is conveniently achieved by the methods described in U.S. Pat. Nos. 4,356, 338, 5,110,776, 5,231,064 and 5,348,643, the entire disclosures of which are incorporated herein by reference. Treatment with phosphorus-containing compounds can readily be accomplished by contacting the porous crystalline material, either alone or in combination with a binder or matrix material, with a solution of an appropriate phosphorus compound, followed by drying and calcining to convert the phosphorus to its oxide form. Contact with the phosphorus-containing compound is generally conducted at a temperature of about 25° C. and about 125° C. for a time between about 15 minutes and about 20 hours. The concentration of the phosphorus in the contact mixture may be between about 0.01 and about 30 wt. %.

After contacting with the phosphorus-containing compound, the porous crystalline material may be dried and calcined to convert the phosphorus to an oxide form. Calcination can be carried out in an inert atmosphere or in the presence of oxygen, for example, in air at a temperature of about 150 to 750° C., preferably about 300 to 500° C., for at least 1 hour, preferably 3–5 hours.

Similar techniques known in the art can be used to incorporate other modifying oxides such as boron-containing compounds, magnesium-containing compounds, calcium-containing compounds, and/or lanthanum-containing compounds into the catalyst of the invention.

Representative phosphorus-containing compounds which may be used to incorporate a phosphorus oxide modifier into the catalyst of the invention are described in the above-referenced International Publication Number WO 98/14415, the disclosure of which is incorporated herein by reference for the purpose of describing those compounds.

The operating conditions employed in the process of the present invention will affect the pseudocumene selectivity, xylene conversion, methanol utilization, and pseudocumene/durene ratio. Methanol utilization as used herein means that methanol in the feed which is converted to a methyl group on a C9 aromatic molecule in the product stream. Such conditions include the temperature, pressure, space velocity, molar ratio of xylenes/methanol in the reactants, and the amount of methanol injections. For example, at xylene/methanol ratios below about 4, it has been demonstrated that both pseudocumene:durene ratio and methanol utilization drop below acceptable levels for commercial use of the process. A drop in methanol utilization has been shown to correspond to an increase in the volume of light ends exiting the process, which is undesirable. Methanol utilization remains fairly constant over the temperature range of the process of the invention, although it has been observed that pseudocumene:durene ratio increases with temperature. Methanol utilization has been discovered to be independent of pseudocumene concentration, and as discussed below, this contributes to the ability to predict 15 to 20% per pass xylene conversion at 25 to 30% methanol utilization for simulated methanol injection in accordance with the process of the invention. In fact, total xylene conversion levels may only be limited by the number of methanol injection points in the apparatus used to carry out the process of the invention. The process in accordance with the invention may achieve on the order of about 7% to about 10% xylene conversion without methanol injection, i.e., in an experimental apparatus as described below with methanol feed but no methanol injection. The addition of water to the feedstream is optional and the molar ratio of water to hydrocarbon in the feedstream has not been shown to have any substantial effect on other process variables.

In embodiments of the invention, the process for the selective production of pseudocumene comprises the steps of (a) reacting a xylene feed in a first reaction step with a first feed comprising methanol under alkylation conditions in the presence of a molecular sieve catalyst; and (b) subsequent to the first reaction step, introducing, via methanol injection or other suitable means, at least one additional feed comprising methanol. The multiple methanol injections of the present invention may obtain at least 15, preferably 20 percent single pass conversion of the xylene feed and at least 25 percent, preferably 30 percent methanol utilization. The process of the invention achieves high selectivity for pseudocumene wherein the pseudocumene content is at least 95 percent of the C9 aromatics fraction as well as at least 90 mole percent of the C9+ fraction. Moreover, pseudocumene/durene ratios of at least 10 and up to 20 or more are obtained by the process of the present invention, which may eliminate the need for further processing steps to purify the pseudocumene product stream.

In embodiments of the invention, a molecular sieve catalyst in accordance with the invention is contacted with a xylene/methanol feedstock with subsequent addition of at least one methanol feed under conditions for effecting vapor-phase methylation. Conditions effective for accomplishing the high pseudocumene selectivity and acceptable xylene conversion rates include a reactor inlet temperature of from about 1000° F. to about 1150° F., preferably from 1050° F. to about 1020° F.; a pressure of from about atmospheric to about 10 atmospheres, preferably from about 1 atmosphere to about 2 atmospheres; a WHSV of from about 0.1 to about 20, preferably from about 0.5 to about 5.0; and a xylene/methanol feed mole ratio of at least about 4:1, preferably at least about 8:1. This process may be conducted in either batch or continuous operation, with the attendant benefits of either operation readily obtainable. The effluent from the xylene methylation process of the invention may be distilled to yield a trimethylbenzene fraction with a very high pseudocumene content, for example 95% or even greater than 99%. Also, in a process scheme where a xylene isomerization reactor is present, the effluents from the xylene isomerization reactor and the process of the invention may be combined for downstream separation. The relatively high purity of pseudocumene attained by the process of the invention reduces, and in some instances eliminates, the need for further purification of the pseudocumene before it is processed to make other products, such as the oxidization of pseudocumene to form trimellitic acid.

EXAMPLES

General

The following non-limiting Examples illustrate the xylene methylation process according to the invention. Fixed bed catalytic testing was conducted using a ½" outside diameter, down-flow reactor contained within a 10" single zone furnace. Upstream of the reactor, two Isco high pressure positive displacement pumps were used to deliver the xylene/methanol mixture and the water, respectively, to a feed vaporizer maintained at 220° C. Laboratory grade methanol and mixed xylenes having a compostion of 25% p-xylene, 25% o-xylene and 50% m-xylene were used. The product distribution was analyzed with an on-line HP-5090 Gas Chromatograph with a 60 m DBWax column and an FID detector. Because the experimental apparatus had only one catalyst bed, staged methanol injection was simulated by diluting 8:1 xylenes/methanol feedstock with increasing amounts of pseudocumene. The negligible amounts of C5− and C10+ products in the process effluent were assumed to have minimal impact on the process of the invention and therefore were not added to the simulated interstage product. It is proposed that the process of the invention obtains 20% per pass xylene conversion at 30% methanol utilization because, as shown below, 30% or more methanol utilization is obtained for each sequential simulated methanol injected step (i.e., for different pseudocumene concentrations) wherein approximately 4% to 5% of the xylenes are converted. Therefore, if the sequential steps were to be lumped into one pass of a multiple sequential methanol injection system, the xylene conversions would be additive. For example, given the experimental xylene conversion results, 5 or more sequential methanol injections would be predicted to yield on the order of 20% or more xylene conversion for a single pass through such an experimental apparatus, at a methanol utilization level of at least 30%.

Example 1

A suitable low activity catalyst in accordance with the process of the invention was prepared by slurrying kaolin clay, 450:1 silica to alumina ratio ZSM-5 crystal, and phosphoric acid with water. The slurry was then spray dried into microsphere having 4% phosphorus and 40% ZSM-5 by weight. The micropheres were hardened by calcination in air at 1100° F.±100° F. Ammonia and residual organics were removed during the calcination step. In order to lower the activity of the catalyst microspheres for methylation of pseudocumene in accordance with the process of the invention, the catalyst microspheres were steamed at 1600° F. for 42 hours.

Example 2

A xylene methylation run utilizing the catalyst prepared in Example 1 was conducted in the experimental unit described above. Approximately 2.0 grams of the phosphorus modified, 40% ZSM-5 catalyst microspheres were loaded into the reactor. A feed stream having 18.12 weight percent water, 2.98 weight percent methanol and 78.90 weight percent xylenes (25% ortho, 25% para, 50% meta and 8:1 xylenes/methanol) was vaporized and fed through the reactor. The furnace temperature was 586° C. and the reactor bed temperature was 574° C. at a weight hourly space velocity of approximately 4. After approximately 8 and ½ hours the product effluent was sampled analyzed by GC. The results for product composition as ascertained by GC analysis, xylene conversion, methanol conversion and utilization, pseudocumene:durene ratio and pseudocumene:C9+ ratio are reported in Table 1.

Example 3

A xylene methylation run utilizing the catalyst prepared in Example 1 was conducted in the experimental unit described above. Approximately 4.0 grams of the 20 phosphorus modified, 40% ZSM-5 catalyst microspheres were loaded into the reactor. A feed stream having 18.12 weight percent water, 2.98 weight percent methanol and 78.90 weight percent xylenes (25% ortho, 25% para, 50% meta and 8:1 xylenes/methanol) was vaporized and fed through the reactor. The furnace temperature was 586° C. and the reactor bed temperature was 586° C. at a weight hourly space velocity of approximately 2. After approximately 8 and ½ hours the product effluent was sampled analyzed by GC. The results are reported in Table 1.

Example 4

A xylene methylation run utilizing the catalyst prepared in Example 1 was conducted in the experimental unit described above. Approximately 4.0 grams of the phosphorus modified, 40% ZSM-5 catalyst microspheres were loaded into the reactor. A feed stream having 18.12 weight percent water, 5.76 weight percent methanol and 76.12 weight percent xylenes (25% ortho, 25% para, 50% meta and 4:1 xylenes/methanol) was vaporized and fed through the reactor. The furnace temperature was 586° C. and the reactor bed temperature was 586° C. at a weight hourly space velocity of approximately 2. After approximately 8 and ½ hours the product effluent was sampled analyzed by GC. The results are reported in Table 1.

Example 5

A xylene methylation run simulating methanol injection by the use of pseudocumene in the feedstock and utilizing the catalyst prepared in Example 1 was conducted in the experimental unit described above. Approximately 4.0 grams of the phosphorus modified, 40% ZSM-5 catalyst microspheres were loaded into the reactor. A feed stream having 18.12 weight percent water, 2.68 weight percent methanol, 71.01 weight percent xylenes (25% ortho, 25% para, 50% meta and 8:1 xylenes/methanol) and 8.19 weight percent pseudocumene was vaporized and fed through the reactor. The furnace temperature was 586° C. and the reactor bed temperature was 586° C. at a weight hourly space velocity of approximately 2. After approximately 8 and ½ hours the product effluent was sampled analyzed by GC. The results are reported in Table 1 and show that in the process according to the invention methanol utilization and xylene conversion are essentially unaffected by 10% pseudocumene concentration in the process feed.

Example 6

A xylene methylation run simulating methanol injection by the use of pseudocumene in the feedstock and utilizing the catalyst prepared in Example 1 was conducted in the experimental unit described above. Approximately 4.0 grams of the phosphorus modified, 40% ZSM-5 catalyst microspheres were loaded into the reactor. A feed stream having 18.12 weight percent water, 2.38 weight percent methanol, 63.40 weight percent xylenes (25% ortho, 25% para, 50% meta and 8:1 xylenes/methanol) and 16.10 weight percent pseudocumene was vaporized and fed through the reactor. The furnace temperature was 586° C. and the reactor bed temperature was 586° C. at a weight hourly space velocity of approximately 2. After approximately 8 and ½ hours the product effluent was sampled analyzed by GC. The results are reported in Table 1 and show that in the process according to the invention methanol utilization and xylene conversion are essentially unaffected by 20% pseudocumene concentration in the process feed.

TABLE I

| Product Comp. Wt. % | Example 2 | Example 3 | Example 4 | Example 5 | Example 6 |
|---|---|---|---|---|---|
| Water | 19.45 | 19.65 | 21.13 | 19.58 | 19.32 |
| C5— | 0.66 | 0.74 | 1.57 | 0.62 | 0.55 |
| Methanol | 0.59 | 0.22 | 0.40 | 0.22 | 0.26 |
| Benzene | 0.03 | 0.04 | 0.06 | 0.04 | 0.05 |
| Toluene | 0.22 | 0.32 | 0.37 | 0.30 | 0.27 |
| Ethylbenzene | 0.02 | 0.02 | 0.03 | 0.02 | 0.02 |
| P-xylene | 17.37 | 16.88 | 15.29 | 15.20 | 13.64 |
| M-xylene | 39.35 | 39.08 | 37.57 | 35.10 | 31.44 |
| O-xylene | 19.5 | 19.32 | 18.49 | 17.38 | 15.55 |
| C9's with BP < Pseudocumene | 0.10 | 0.11 | 0.17 | 0.37 | 0.64 |
| Pseudocumene | 2.53 | 3.40 | 4.52 | 10.66 | 17.78 |
| BP > Pseudocumene – durene | 0.05 | 0.05 | 0.09 | 0.37 | 0.33 |
| Durene | 0.14 | 0.17 | 0.31 | 0.15 | 0.14 |
| TOTAL | 100.0 | 100.0 | 100.0 | 100.0 | 100.0 |
| Methanol Conversion (%) | 80.3 | 92.5 | 93.0 | 91.8 | 88.9 |
| Xylene Conversion (%) | 3.4 | 4.6 | 6.3 | 4.7 | 4.4 |
| Methanol Utilization (%) | 28 | 33 | 23 | 32 | 32 |
| Pseudocumene/durene | 17.5 | 20.6 | 14.5 | 19.6 | 17.6 |
| Pseudocumene/C9 + (%) | 89.7 | 91.2 | 88.9 | 92.3 | 94.1 |

The results listed above demonstrate that high pseudocumene selectivity can be achieved by the xylene methylation process according to the invention, while maintaining acceptable rates of xylene conversion (3.4% to 6.3%, as shown above).

The results of Table 1 also demonstrate that the xylene methylation process of the present invention produces an effluent stream that can be easily processed by simple distillation to remove unconverted feed and other process by products and yield a high purity pseudocumene product.

What is claimed is:

1. A process for the selective production of pseudocumene which comprises the steps of:

reacting a xylene feed with a first feed comprising methanol in a first reaction step to produce a first reaction effluent; and subsequent to said first reaction step, introducing at least a second feed comprising methanol into said first reaction effluent and reacting said second feed with said first reaction effluent in a second reaction step, wherein the first and second reaction steps are conducted in the presence of a molecular sieve catalyst having a alpha value of less than 1 under alkylation conditions including a temperature of about 1000° F. to about 1150° F. a pressure from about 1 to about 2 atmospheres, a weight hourly space velocity between about 0.5 and about 5.0, so that said process attains at least 15 percent single pass conversion of the xylene feed and at least 25 percent methanol utilization and produces a product stream in which pseudocumene comprises at least 90 mole percent of the $C_9+$ fraction and which has a pseudocumene to durene ratio of at least 10.

2. The process of claim 1, wherein said molecular sieve catalyst has undergone prior treatment with steam at a temperature of 1600° F. or less for between about 1 hour and about forty eight hours.

3. The process of claim 2 wherein said molecular siere is an aluminosilicate ZSM-5 zeolite.

4. The process of claim 3 wherein said catalyst has a silica to alumina molar ratio of at least 250.

5. The process of claim 4 wherein said catalyst comprises from about 30% to about 65% by weight ZSM-5.

6. The process of claim 5 wherein said catalyst comprises at least about 3% by weight phosphorus.

7. The process of claim 1 wherein said xylene feed comprises at least two xylene isomers.

8. The process of claim 1, wherein said alkylation conditions include a molar ratio of xylene to methanol of at least about 4:1.

9. The process of claim 8, wherein said alkylation conditions include a molar ratio of xylene to methanol of at least about 8:1.

* * * * *